US006284776B1

(12) United States Patent
Meltzer

(10) Patent No.: US 6,284,776 B1
(45) Date of Patent: Sep. 4, 2001

(54) METHOD FOR TREATING DISEASED-RELATED OR DRUG-INDUCED DYSKINESIAS

(76) Inventor: Leonard T. Meltzer, 2906 Renfrew, Ann Arbor, MI (US) 48105

(*) Notice: Subject to any disclaimer, the term of this patent is extended or adjusted under 35 U.S.C. 154(b) by 0 days.

(21) Appl. No.: 09/485,348
(22) PCT Filed: Sep. 16, 1998
(86) PCT No.: PCT/US98/19357
§ 371 Date: Feb. 7, 2000
§ 102(e) Date: Feb. 7, 2000
(87) PCT Pub. No.: WO99/21539
PCT Pub. Date: May 6, 1999

Related U.S. Application Data

(60) Provisional application No. 60/063,156, filed on Oct. 24, 1997.

(51) Int. Cl.[7] .................................................. A61K 31/445
(52) U.S. Cl. ............................................................ 514/326
(58) Field of Search .............................................. 514/326

(56) References Cited

U.S. PATENT DOCUMENTS

| 3,509,164 | 4/1970 | Carron et al. ...................... 260/294.7 |
| 5,272,160 | 12/1993 | Chenard ................................ 514/327 |
| 5,364,867 | * 11/1994 | Dehaven et al. ..................... 514/326 |
| 5,547,963 | 8/1996 | Poindron et al. .................... 514/317 |

FOREIGN PATENT DOCUMENTS

| 0648744 | 4/1995 | (EP) . | |
| 91/06297 | * 5/1991 | (WO) | ................................... 514/348 |
| 93/00313 | * 1/1993 | (WO) | ................................... 514/346 |
| 93/22310 | * 11/1993 | (WO) | ................................... 514/348 |
| 96/37226 | * 11/1996 | (WO) | ................................... 514/348 |
| 9723214 | 7/1997 | (WO) . | |

OTHER PUBLICATIONS

Costall et al, J. Pharm., Pharmac., vol. 30, pp. 693–696, 1978.*
Merck Index, p. 785, 1996.*
A.B. Joseph and R.R. Young, editors, "Movement Disorders in Neurology and Neuropsychiatry", Blackwell Scientific Publications, 1992.
Monyer et al., "Heteromeric NMDA Receptors: Molecular and Functional Distinction of Subtypes", *Science*, vol. 256, 1992, pp. 1217–1221.
Muir and Lees, "Clinical Experience With Excitatory Amino Acid Antagonist Drugs", *Stroke*, vol. 26, No. 3, 1995, pp. 503–513.

* cited by examiner

*Primary Examiner*—James H. Reamer
(74) *Attorney, Agent, or Firm*—Elizabeth M. Anderson; Charles W. Ashbrook

(57) ABSTRACT

Dyskinesias in humans are treated by administering a therapeutically effective dose of an NR1A/2B site-selective NMDA receptor antagonist compound to a human suffering therefrom.

7 Claims, 4 Drawing Sheets

METHOD FOR TREATING DISEASED-RELATED OR DRUG-INDUCED DYSKINESIAS

This application is a national stage of PCT/US98/19357 filed Sep. 16, 1998 which claims benefit of Provisional Application Ser. No. 60/063,156 filed Oct. 24, 1997.

BACKGROUND OF THE INVENTION

1. Field of the Invention

This invention relates to a method for treating disease-related or drug-induced dyskinesias.

2. Related Background Art

Dyskinesias are debilitating motor movements that can be caused by a neurological disease, or can be drug-induced. See, for example, A. B. Joseph and R. R. Young, Movement Disorders in Neurology and Neuropsychiatry (Blackwell Scientific Publications, 1992), the disclosure of which is incorporated by reference herein. Disease-related dyskinesias can result from a wide range of conditions, including Wilson's disease, Huntington's disease and Sydenham's chores Drug-induced dyskinesias have been attributed to administration of many drugs, including drugs used in treatment of Parkinson's disease, e.g., L-DOPA, nonselective dopamine-agonists (DA-agonists), as well as DA-agonists selective for the D1, D2, D3, D4 and D5 subtypes of the dopamine receptor; and DA antagonists, especially in the case of prolonged administration of antipsychotic agents, which leads to tardive dyskinesias.

Drugs which act as non-selective antagonists of the N-methyl-D-aspartate (NMDA) receptor have been shown to decrease dyskinesias induced by administration of L-DOPA to primates suffering from 1,2,3,6-tetrahydro-1-methyl4-phenylpyridine (MPTP)-induced Parkinson's disease. The NMDA receptor comprises a NR1 subunit in combination with one or more of the NR2 subunits, NR2B, NR2C or NR2D, as disclosed in Monyer et al., Science, Vol. 256, pages 1217–1221 (1992). K. W. Muir and K. R. Lees, Stroke, Vol. 26, pages 503–513 (1995), discloses that administration of NMDA receptor antagonists that are NR1A/2B-site-selective leads to reduced psychotomimetic side-effects than administration of non-selective antagonists. S. M. Papa and T. N. Chase, Annals of Neurology, Vol. 39, pages 574–578 (1996), discloses that administration of the drug LY235959, available from Eli Lilly, Inc., reduced the severity of dyskinesia in monkeys being treated with L-DOPA. However, LY235959 is a non-selective NMDA receptor antagonist. It is not obvious from this work which subtype of the NMDA receptor is responsible for the antidyskinetic effect.

PCT International Publication No. WO 96/37226 discloses treatment of Parkinsons disease with a combination of site-selective NMDA receptor antagonist compounds and L-DOPA. Administration of the antagonist compounds allowed use of lower amounts of L-DOPA. However, there is no suggestion that NR1A/2B site-selective NMDA receptor antagonist compounds could be administered to reduce the side effects accompanying normal doses of L-DOPA.

Methods of treatment of dyskinesias with compounds which are NR1A/2B-site-selective NMDA receptor antagonists would be desirable.

SUMMARY OF THE INVENTION

This invention is directed to a method for treating dyskinesias, said method comprising administering to a human suffering therefrom a therapeutically effective amount of a NR1A/2B-site-selective NMDA receptor antagonist compound.

In a preferred embodiment of this invention, the compound is

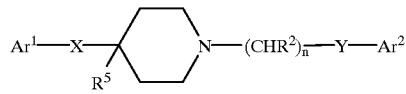

or a pharmaceutically acceptable salt thereof wherein $Ar^1$ and $Ar^2$ are independently aryl or a heteroaryl group, either of which may be independently substituted by one to three of hydroxy, alkyl, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

X is $—(CHR^3)_m—$, wherein each $R^3$ is independently hydrogen, hydroxy, or a lower alkyl group having 1 to 6 carbon atoms; and m is 0 or 1;

each $R^2$ is independently hydrogen, hydroxy or a lower alkyl group having 1 to 6 carbon atoms;

n is 1,2,3 or 4;

Y is $C≡C$, O, $SO_p$ wherein p is 0, 1 or 2, $NR^4$ wherein $R^4$ is hydrogen or a lower alkyl group having 1 to 6 carbon atoms, or a single bond; and $R^5$ is hydrogen or hydroxy.

In another preferred embodiment, the compound has a structure selected from those listed below, their stereoisomers, and their pharmaceutically acceptable salts:

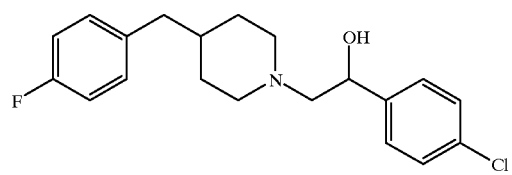

α-(4-chlorophenyl)-4-[(4-fluorophenyl)methyl]-1-piperidineethanol;

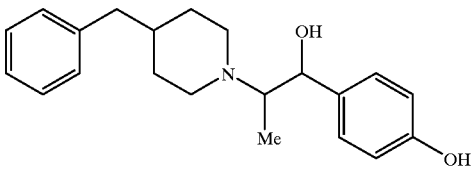

α-(4-hydroxyphenyl)-β-methyl-4-(phenylmethyl)-1-piperidineethanol;

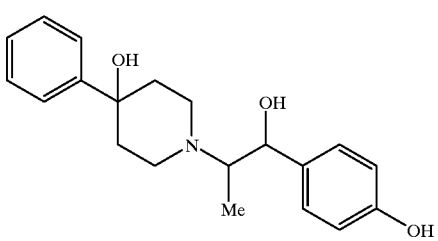

4-hydroxy-α-(4-hydroxyphenyl)-β-methyl-4-phenyl-1-piperidineethanol;

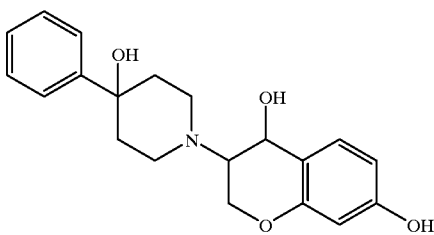

3-[4-(4-phenyl)-4-hydroxypiperidin-1-yl]chroman4,7-diol; and

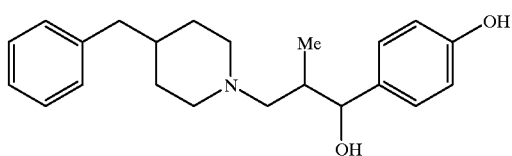

α-(4-hydroxyphenyl)-β-methyl(phenylmethyl)-1-piperidinepropanol.

DETAILED DESCRIPTION OF THE INVENTION

Figure 1:
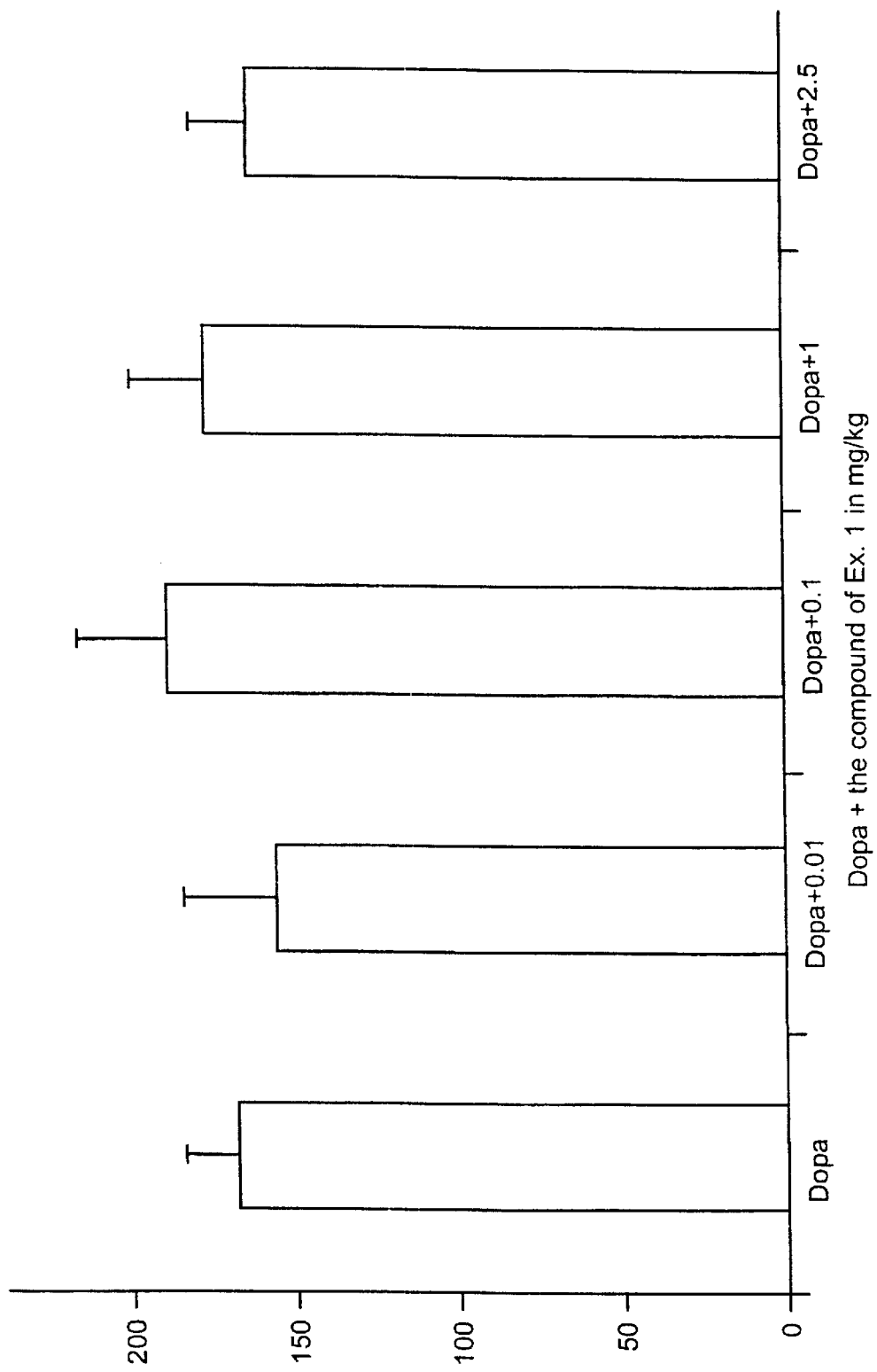
FIG. 1 is a graph showing the duration of L-DOPA response for L-DOPA in combination with varying doses of a NR1A/2B site-selective NMDA antagonist.

In the method of this invention, dyskinesias are treated by administration of a therapeutically effective amount of a NR1A/2B-site-selective NMDA receptor antagonist compound. Preferably, this invention employs a compound having the structure:

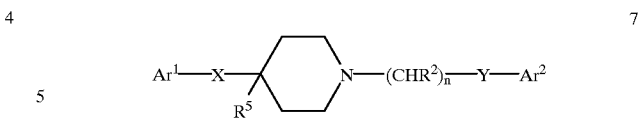

or a stereoisomer or pharmaceutically acceptable salt thereof wherein $Ar^1$ and $Ar^2$ are independently aryl or a heteroaryl group, either of which may be independently substituted by one to three of hydroxy, alkyl, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;

X is $-(CHR^3)_m-$, wherein each $R^3$ is independently hydrogen, hydroxy or a lower alkyl group having 1 to 6 carbon atoms; and m is 0 or 1;

each $R^2$ is independently hydrogen, hydroxy or a lower alkyl group having 1 to 6 carbon atoms;

n is 1,2,3 or 4;

Y is $C{\equiv}C$, O, $SO_p$ wherein p is 0, 1 or 2, $NR^4$ wherein $R^4$ is hydrogen or a lower alkyl group having 1 to 6 carbon atoms, or a single bond; and $R^5$ is hydrogen or hydroxy, which are disclosed in PCT International Publication Nos. WO 97/23216 and WO 97/23214, the disclosures of which are incorporated by reference herein.

In another preferred embodiment of this invention, the compound administered is selected from the compounds having the structures and names listed below, their stereoisomers, and their pharmaceutically acceptable salts:

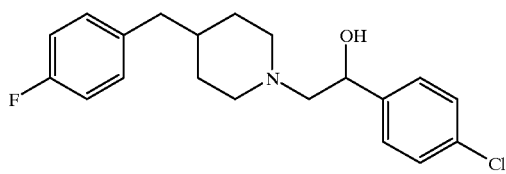

α-(4-chlorophenyl)4-[(4fluorophenyl)methyl]-1-piperidineethanol (Eliprodil, available from Synthelabo, Inc., and disclosed in U.S. Pat. No. 5,547,963)

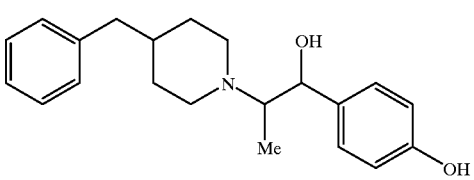

α-(4-hydroxyphenyl)-β-methyl-4-(phenylmethyl)-1-piperidineethanol (Ifenprodil, available from Synthelabo, Inc., and disclosed in U.S. Pat. No. 3,509,164)

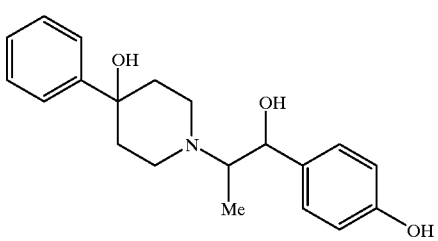

4-hydroxy-α-(4-hydroxyphenyl)-β-methyl-4-phenyl-1-piperidineethanol (optically active form CP-101,606, available from Pfizer, Inc., and disclosed in U.S. Pat. No. 5,272,160).

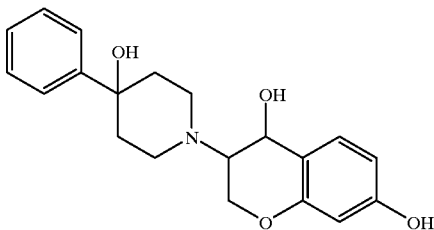

3-[4-(4-phenyl)4-hydroxypiperidin-1-yl]-chroman4,7-diol (optically active from CP-283,097, available from Pfizer, Inc.)

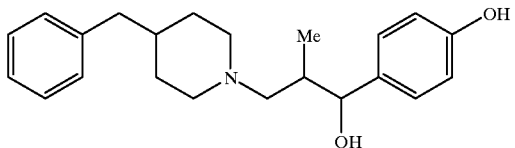

α-(4-hydroxyphenyl)-β-methyl4(phenylmethyl)-1-piperidinepropanol (optically active form Ro 25-6981, available from Hoffmann-La Roche, and disclosed in European Patent Application No. EP 648,744).

The most preferred compounds for administration in the method of this invention are 1-[2-(4-hydroxyphenoxy)ethyl]-4-hydroxy-4-(4-methylbenzyl) piperidine hydrochloride, which has the following structure:

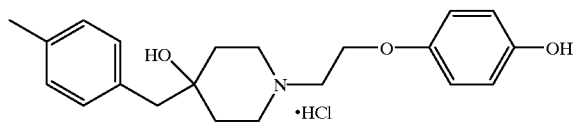

and 1-[2-(4-Hydroxyphenoxy)ethyl]-4-(4-fluorobenzyl) 4hydroxy-piperidine hydrochloride, which has the following structure:

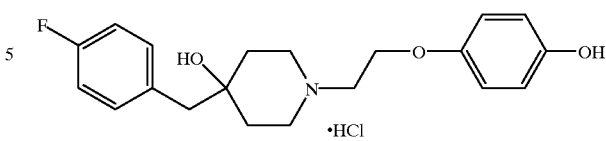

and CP-101,606, [S-(R*,R*)]-4hydroxy-α-(4-hydroxyphenyl)-β-methyl-4-phenyl-1-piperidineethanol, which has the following structure:

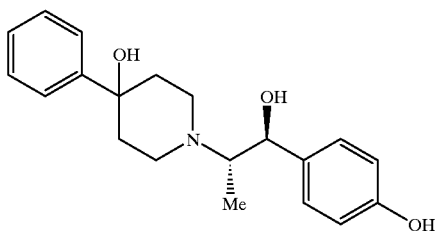

and is described in PCT Application No. WO 96/37226, the disclosure of which is incorporated by reference herein.

Also included within the scope of the present invention is the use of the non-toxic pharmaceutically acceptable salts of the compounds described herein. Acid addition salts are formed by mixing a solution of the particular compound used in the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Suitable dosage levels in the method of this invention for oral administration range from about 100 mg/dose to about 1000 mg/dose. For subcutaneous administration, the suitable level is from about 1 mg/dose to about 200 mg/dose. The examples which follow are intended as illustrations of certain preferred embodiments of the invention, and no limitation of the invention is implied.

EXAMPLE 1

1-[2-(4-Hydroxyphenoxy)ethyl]-4hydroxy-4-(4-methylbenzyl)piperidine hydrochloride

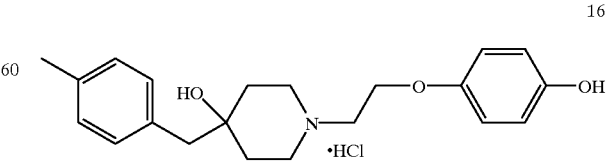

A) 1-Benzyl-4-hydroxy4-(4-methylbenzyl)piperidine. To a 250mL three-necked round-bottomed flask was added 2.31 g of Mg tunings and 15 mL of anhydrous THF under $N_2$. To which was added dropwise a solution of 1,2-dibromoethane (0.489 g, 2.65 mmol) in 5 mL of THF at rt. After addition, THF was removed, and the residue was rinsed with THF (2×5 mL). To this residue was added dropwise a solution of 4-methylbenzyl chloride (13.0 g, 92.6 mmol) in 50 mL of THF at 0° C. After addition, the solution was allowed to stir at rt for 2 h and another 50 mL of THF was added. After cooling down to −35° C. to 40° C., a solution of 4-benzylpiperidone (5.0 g, 26.5 mmol) in 20 mL of THF was added dropwise. After the addition was complete, the reaction mixture was allowed to stir at rt for 3 h and stand overnight. To this reaction mixture was added 100 mL of saturated $NH_4Cl$ aqueous solution at 0° C. and then extracted with dichloromethane (2×50 mL). The combined organic phase was evaporated in vacuo to give an oil, which was redissolved into 200 mL of dichloromethane and washed with saturated $NH_4Cl$ aqueous solution (2×30 mL) and brine (50 mL), and then dried over sodium sulfate. Evaporation of solvent followed by flash chromatography (EtOAc $R_f$=0.25), giving 7.5 g (96%) of the product as a pale yellow oil.

$^1$H NMR ($CDCl_3$): 1.476 (m, 2 H), 1.725 (m, 2 H), 2.046 (s, 1 H), 2.323 (m, 5 H), 2.611 (m, 2 H), 2.713 (s, 2 H), 3.505 (s, 2 H), 7.086 (m, 4 H), 7.299 (m, 5 H).

B) 4-Hydroxy4-(4-methylbenzyl)piperidine hydrochloride. A mixture of 1-benzyl-4-(4-methylbenzyl)-4-hydroxypiperidine (2.8 g, 9.5 mmol) and 700 mg of 10% Pd/C in 100 mL of 95% ethanol was hydrogenated at 50 psi for overnight. The catalyst was removed through a short column of celite (10 g) and washed with methanol (3×15 mL). To the filtrate was added 12 mL of 1M HCl in methanol. Evaporation of methanol gave a residue, to which was added 30 mL of ether. The mixture was stirred at rt for 2 days. A white solid was collected by filtration, giving 2.1 g (92%) of the title product: mp 183–185° C.

$^1$H NMR ($CDCl_3$): 1.680 (m, 2 H), 2.097 (m, 2 H), 2.338 (s, 3 H), 2.783 (s, 2 H), 3.241 (m, 5 H), 7.049 (d, J=7.5 Hz, 2 H), 7.142 (d, J=7.5 Hz, 2 H), 9.30 (brs, 1 H), 9.515 (brs, 1 H).

C) 1-[2-(4-Benzyloxyphenoxy)ethyl]-4-hydroxy4-(4-methylbenzyl) piperidine hydrochloride. A mixture of 2-(4-benzyloxyphenoxy)ethyl bromide (368 mg, 1.2 mmol), 4(4-methylbenzyl)4hydroxypiperidine hydrochloride (290 mg, 1.2 mmol), potassium carbonate (414 mg, 3 mmol) in 30 mL of acetonitrile was allowed to reflux for 12 h. The inorganic salt was removed through a short column of silica gel and washed with ethyl acetate (3×25 mL). The combined filtrate was evaporated in vacuo to give a crude mixture, which was purified by flash chromatography (5% methanol in ethyl acetate), giving a pale yellow oil, which was dissolved into methanol (10 mL), to which was added 4 mL of 1 M HCl in methanol. The resulting solution was allowed to stir at rt for 10 min, and methanol was evaporated in vacuo to give a residue, to which 50 mL of ether was added. The resulting mixture was stirred overnight. A white solid was collected by filtration and dried in vacuo, giving 420 mg (75%) of the title product: mp 179–181° C.

$^1$H NMR ($CDCl_3$): 1.605 (s, 2 H), 1.725 (d, J=14.1 Hz, 2 H), 2.332 (s, 3 H), 2.453 (m, 2 H), 2.809 (s, 2 H), 3.221 (m, 2 H), 3.361 (s, 1 H), 3.464 (d, J=8.4 Hz, 2 H), 4.488 (s, 2 H), 5.005 (s, 2 H), 6.820 (d, J=9.0 Hz, 2 H), 6.904 (d, J=9.0 Hz, 2 H), 7.077 (d, J=7.5 Hz, 2 H), 7.166 (d, J=7.5 Hz,2H), 7.376 (m, 5 H), 12.4 (bs, 1 H).

D) 1-[2-(4-Hydroxyphenoxy)ethyl]-1-hydroxy-4-(4-methylbenzyl)piperidine hydrochloride. To a solution of 1-[2-(4-benzyloxyphenoxy)ethyl]-4-hydroxy-4-(4-methylbenzyl)piperidine hydrochloride (0.25 g, 0.53 mmol) in 30 mL of methanol was added 62.5 mg of 20% $Pd(OH)_2$. The resulting mixture was hydrogenated at 20 psi of hydrogen for 3 h. The catalyst was removed through a short column of celite (5 g) and washed with methanol (3×15 mL). Methanol was evaporated in vacuo to give a residue, to which 50 mL of ether was added. The resulting mixture was stirred overnight. A white solid was collected by filtration and dried in vacuo, giving 200 mg (100%) of the title product: mp 133–135° C.

$^1$H NMR ($CD_3OD$): 1.58 (m, 2 H), 1.75 (m, 2 H), 2.119 (s, 3 H), 2.615 (s, 2 H), 3.20–3.30 (m, 6 H), 4.056 (m, 2 H), 6.528 (d, J=9.0 Hz, 2 H), 6.645 (d, J=9.0Hz, 2 H), 6.938 (s, 4 H).

EXAMPLE 2

1-[2-(4-Hydroxyphenoxy)ethyl]-4-(4-fluorobenzyl)-4-hydroxy-piperidine hydrochloride

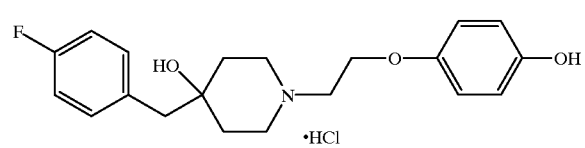

A) 1-[2-(4-Benzyloxyphenoxy)ethyl]-4-(4-fluorobenzyl)-4-hydroxypiperidine. A mixture of 2-(4-benzoxyphenoxy) ethyl bromide (1.075 g, 3.5 mmol), 4-(4-fluorobenzyl)-4-hydroxypiperidine (0.778 g, 3.7 mmol), potassium carbonate (1.28 g, 9.25 mmol) in 50 mL of acetonitrile was allowed to reflux for 12 h. The inorganic salt was removed through a short column of silica gel and washed with ethyl acetate (3×25 mL). The combined filtrate was evaporated in vacuo to give a crude product, which was purified by flash chromatography (5% methanol in ethyl acetate), giving 0.8 g (53%) of the title compound as a pale yellow oil.

$^1$H NMR ($CDCl_3$) 1.544 (m, 2 H), 1.80 (m, 2 H), 2.50 (m, 2 H), 2.834 (m, 3 H), 3.484 (s, 4 H), 4.079 (t, J=4.8 Hz, 2 H), 5.008 (s, 2 H), 6.810 (d, J=9.0 Hz, 2 H), 6.878 (d, J=9.0 Hz, 2 H), 6.997 (m, 2 H), 7.135 (m, 2 H), 7.350 (m, 5 H).

B) 1-[2-(4-Hydroxyphenoxy)ethyl]-4-(4-fluorobenzyl)-4-hydroxypiperidine hydrochloride. To a solution of 1-[2-(4-benzyloxyphenoxy)ethyl]-4-(4-fluorobenzyl-4-hydroxypiperidine (0.8 g, 1.8 mmol) in 25 mL of methanol was added 200 mg of 20% $Pd(OH)_2$. The resulting mixture was hydrogenated at 20 psi of hydrogen for 3 h. The catalyst was removed through a short column of celite (5 g) and washed with methanol (3×15 mL), to which was added 4 mL of 1 M HCl in methanol. The resulting solution was allowed to stir at rt for 10 min. and methanol was evaporated in vacuo to give a residue, to which 50 mL of ether was added. The resulting mixture was stirred overnight. A white solid was collected by filtration and dried in vacuo, giving 550 mg (80%) of the title compound: mp 128–130° C.

$^1$H NMR ($CD_3OD$): 1.732 (m, 2 H), 1.935 (m, 2 H), 2.825 (m, 2 H), 3.328 (m, 2 H), 3.486 (m, 4 H), 4.265 (s, 2 H), 6.719 (m, 2 H), 6.840 (m, 2 H), 7.033 (m, 2 H), 7.238 (m, 2 H). Anal. Calcd for $C_{20}H_{25}ClFNO_3 \cdot 0.5H_2O$: C, 61.46; H6.70; N, 3.58. Found: C, 61.50; H, 6.64; N, 3.59.

EXAMPLE 3

Administration of L-DOPA and the Compound of Example 1 to MPTP-Treated Monkeys

The subjects were 6 cynomolgus monkeys that had stable Parkinson signs induced by treatment with 0.5 mg/kg 1,2, 3,6-tetrahydro-1-methyl-4-phenylpyridine (MPTP) once weekly until development of stable signs occurred. Six weeks after MPTP treatment ended, daily L-DOPA administration was performed for 3–4 weeks until dyskinetic movements had been induced. The treatment dose of L-DOPA was adjusted for each individual monkey. The therapeutic anti-Parkinsonian effect, as well as the dyskinetic effect is different for each monkey. The dose of L-DOPA used was what was effective for each animal. In response to L-DOPA, the monkeys show the expected therapeutic response, i.e., improved motor function, as well as motor side-effects and dyskinesias, that are observed in humans suffering from idiopathic Parkinson's disease.

Figure 2:
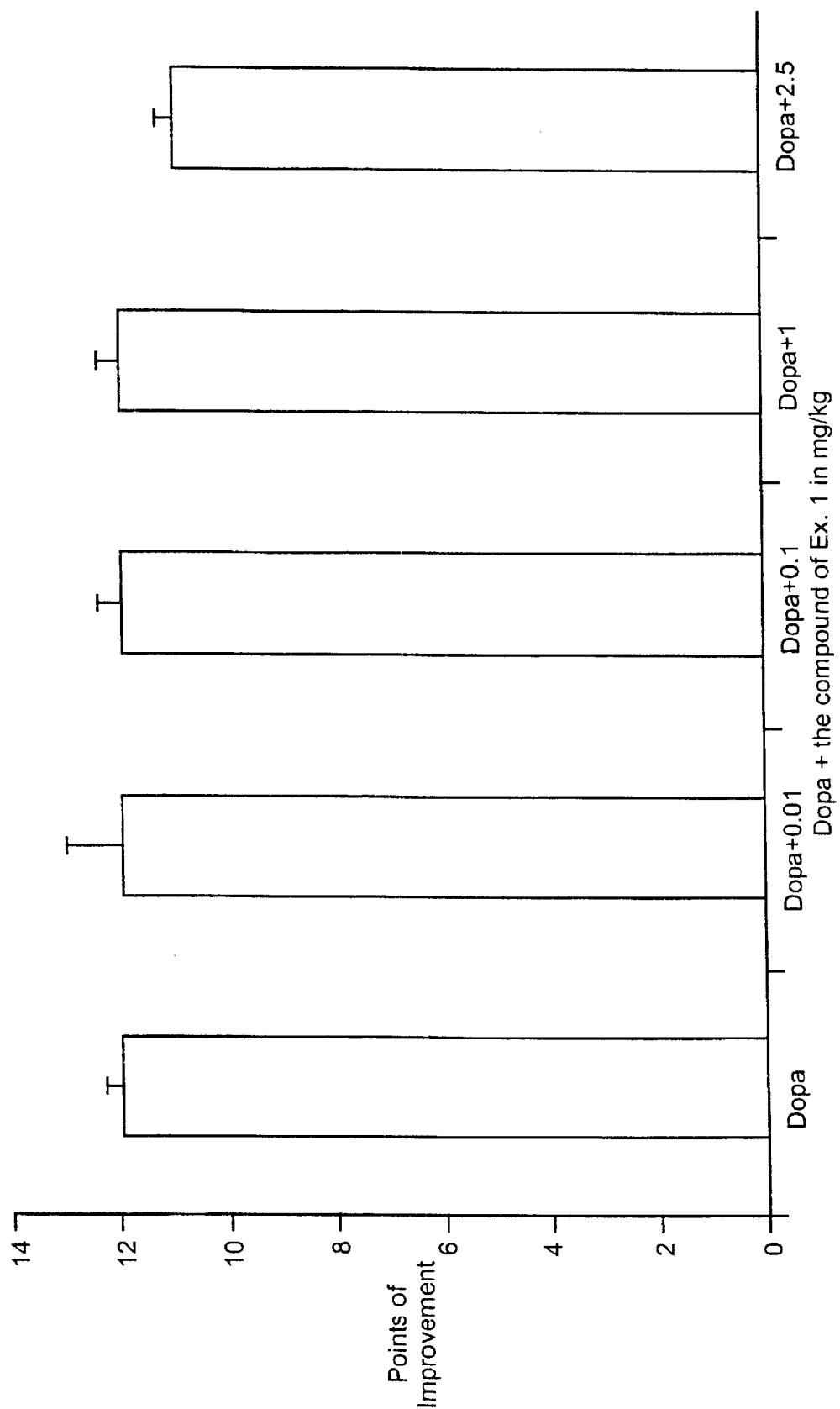
FIG. 2 is a graph showing the magnitude of the anti-Parkinsonian response for L-DOPA in combination with varying doses of a NR1A/2B site-selective NMDA antagonist.
Figure 3:
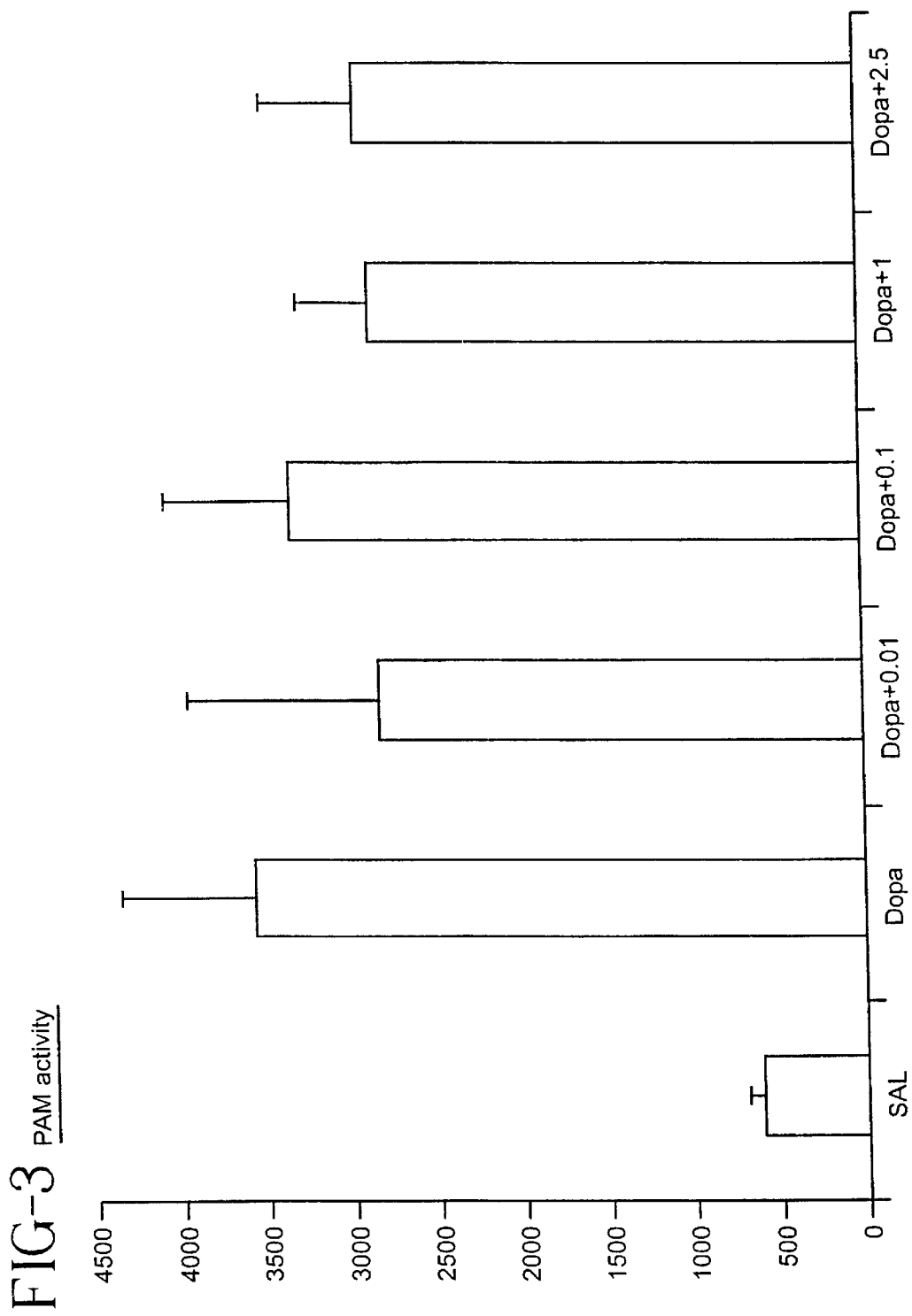
FIG. 3 is a graph showing the magnitude of locomotor activity for L-DOPA in combination with varying doses of a NR1A/2B site-selective NMDA antagonist.
Figure 4:
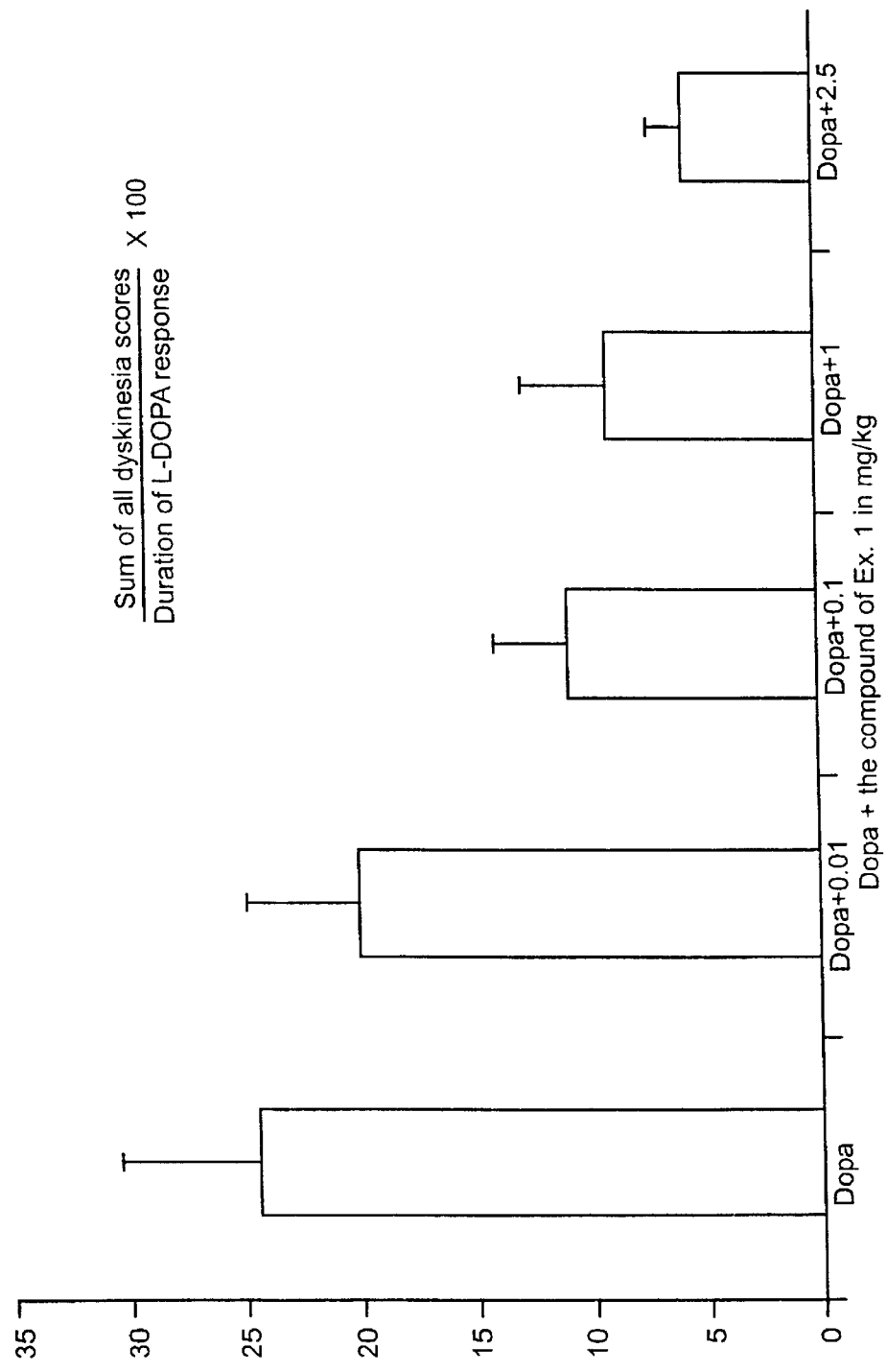
FIG. 4 is a graph showing the sum of all dyskinesia scores as a percentage of the duration of L-DOPA response for L-DOPA in combination with varying doses of a NR1A/2B site-selective NMDA antagonist.

The behavioral effects of L-DOPA alone and in combination with the compound of Example 1 were determined. Both compounds were administered subcutaneously (SC). When co-administered with an effective dose of L-DOPA, the compound of Example 1 at levels of 0.01, 0.1, 1.0 and 2.5 mg/kg SC did not alter the duration in minutes of the L-DOPA-induced behavioral response, as shown in FIG. 1. The magnitude of the peak anti-Parkinsonian response, in terms of points on an improvement scale response, was also unaffected, as shown in FIG. 2, as was locomotor activity, as measured by activity monitors, as shown in FIG. 3. Administration of the compound of Example I reduced, in a dose-response manner, the induction of the L-DOPA-induced dyskinesias, as shown in FIG. 4. Thus, the monkeys retained the therapeutic effects of the L-DOPA, but experienced lessened dyskinetic side-effects.

Other variations and modifications of this invention will be obvious to those skilled in this art This invention is not limited except as set forth in the following claims.

What is claimed is:

1. A method for treating dyskinesias, said method comprising administering to a human suffering therefrom a therapeutically effective amount of a NR1A/2B site-selective NMDA receptor antagonist compound.

2. The method of claim 1, wherein the compound administered has the structure (18):

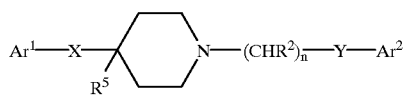

or a stereoisomer or pharmaceutically acceptable salt thereof wherein
   $Ar^1$ and $Ar^2$ are independently aryl or a heteroaryl group, either of which may be independently substituted by one to three of hydroxy, alkyl, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group;
   X is —$(CHR^3)_m$—, wherein each $R^3$ is independently hydrogen, hydroxy or a lower alkyl group having 1 to 6 carbon atoms; and m is 0 or 1;
   each $R^2$ is independently hydrogen, hydroxy or a lower alkyl having 1 to 6 carbon atoms;
   n is 1 or 2;
   each $R^2$ is independently hydrogen, hydroxy or a lower alkyl having 1 to 6 carbon atoms;
   Y is C≡C, O, $SO_p$ wherein p is 0, 1 or 2, $NR^4$ wherein $R^4$ is hydrogen or a lower alkyl group having 1 to 6 carbon atoms, or a single bond;
   $R^5$ is hydrogen of hydroxy; and
   provided $Ar^2$ is substituted by at least one of hydroxy, alkyl, halogen, nitro, cyano, carboxaldehyde, aldehyde oxime, lower alkoxy carbonylmethyl, hydroxy lower alkyl, aminocarbonylmethyl, hydrazinocarbonylmethyl, acetamido, aryl, aralkyl, amino, a halogenated alkyl group, a lower alkyl amino group or a lower alkoxy group.

3. The method of claim 1, wherein the compound is selected from the group consisting of

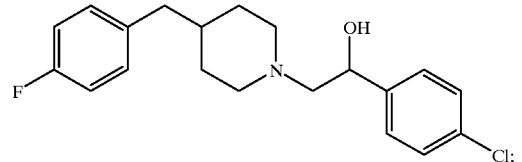

19

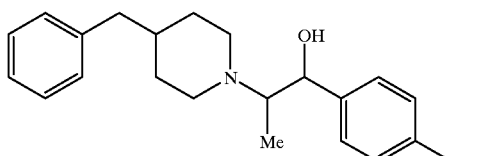

20

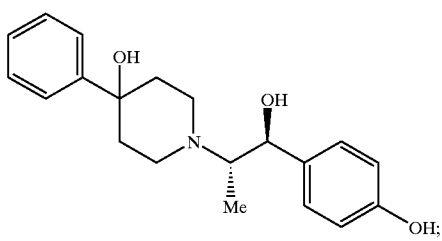

21

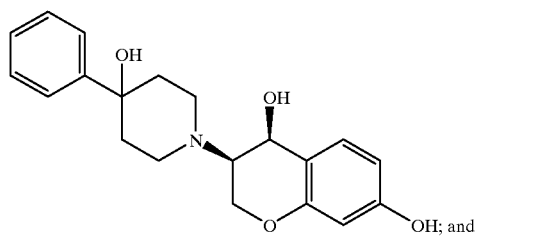

22

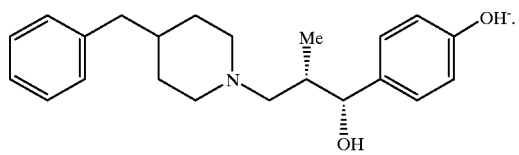

23

4. The method of claim 2 wherein the compound administered is 1-4-hydroxy-4-(4methylbenzyl)piperidine hydrochloride.

5. The method of claim 2 wherein the compound administered is 1-4-(4-fluorobenzyl)-4-hydroxy-piperidine hydrochloride.

6. The method of claim 3, wherein the compound is [S-(R*,R*)]-4-hydroxy-α-(4-hydroxyphenyl)-β-methyl-4phenyl-1-piperidineethanol.

7. A method for reducing dyskinesias in treatment Parkinson's disease, said method comprising administering to a human suffering therefrom a therapeutically effective amount of a NR1A/2B site-selective NMDA receptor antagonist compound.

* * * * *